United States Patent [19]

Sekii et al.

[11] Patent Number: 5,080,106

[45] Date of Patent: Jan. 14, 1992

[54] APPARATUS FOR MEASURING CARDIAC OUTPUT

[75] Inventors: Shigekazu Sekii; Kohji Tsuchida; Yoshio Ishitsu, all of Kanagawa, Japan

[73] Assignee: Terumo Kabushiki Kaisha, Tokyo, Japan

[21] Appl. No.: 463,143

[22] Filed: Jan. 9, 1990

[30] Foreign Application Priority Data

Jan. 13, 1989 [JP] Japan .................................. 1-4717

[51] Int. Cl.⁵ .............................................. A61B 5/02
[52] U.S. Cl. .................................... 128/692; 128/691; 128/736; 73/204.17; 73/204.23
[58] Field of Search ................ 128/419 PG, 691, 692, 128/713, 736; 73/204.17, 204.23

[56] References Cited

U.S. PATENT DOCUMENTS

| | | | |
|---|---|---|---|
| 3,438,253 | 11/1966 | Kuether et al. | 73/204 |
| 3,595,079 | 7/1971 | Grahn. | |
| 3,678,922 | 7/1972 | Phillips et al. . | |
| 3,789,831 | 2/1974 | Kopaniky et al. . | |
| 3,820,530 | 6/1974 | Gilford et al. . | |
| 3,995,623 | 12/1976 | Blake . | |
| 4,004,576 | 1/1977 | Gahwiler et al. . | |
| 4,035,622 | 7/1977 | Obermajer . | |
| 4,230,126 | 10/1980 | Elings | 128/671 |
| 4,240,441 | 12/1980 | Khalil . | |
| 4,380,237 | 4/1983 | Newbower . | |
| 4,502,488 | 3/1985 | Degironimo et al. | 128/692 |
| 4,542,748 | 9/1985 | Roy | 128/713 |
| 4,572,206 | 2/1986 | Geddes et al. . | |
| 4,595,015 | 6/1986 | Jansen et al. . | |
| 4,621,646 | 11/1986 | Bryant . | |
| 4,632,125 | 12/1986 | Webler et al. . | |
| 4,685,470 | 8/1987 | Sekii et al. . | |
| 4,841,981 | 6/1989 | Tanabe et al. | 128/736 |
| 4,858,615 | 8/1989 | Meinema | 128/736 |
| 4,901,734 | 2/1990 | Griffin et al. | 128/692 |

FOREIGN PATENT DOCUMENTS

| | | |
|---|---|---|
| 0182363 | 5/1986 | European Pat. Off. . |
| 0354958 | 9/1988 | European Pat. Off. . |
| 43-27683 | 11/1968 | Japan . |
| 51-10690 | 1/1976 | Japan . |
| 51-185 | 5/1976 | Japan . |
| 54-55144 | 5/1979 | Japan . |
| 57-182656 | 11/1982 | Japan . |
| 57-61413 | 12/1982 | Japan . |
| 61-125329 | 6/1986 | Japan . |
| WO88/06424 | 9/1988 | PCT Int'l Appl. . |

OTHER PUBLICATIONS

Proceedings of the Ninth Annual Symposium on Computer Applications in Medical Care, Baltimore, 10th-13th Nov. 1985, pp. 41-44; R. B. Dew: "Personal Computer System for Automatic Coronary Venous Flow Measurement".

Medical and Biological Engineering, vol. 11, No. 2, 3/73, pp. 201-205, Stevenage, Herts, GB; A. L. Delaunois: "Thermal Method for Continuous Blood-Velocity Measurements in Large Blood Vessels, and Cardiac-Output Determination".

Measurement of Blood Flow, Tissue PO, and Tissue PCO, Continuously and Simultaneously in the Same Structure of the Brain; J. Seylaz et al; 2200 Medical & Biological Engineering & Computing; Jan. 1979, vol. 17, No. 1, pp. 19-21, 24.

*Primary Examiner*—Lee S. Cohen
*Assistant Examiner*—Krista M. Pfaffle
*Attorney, Agent, or Firm*—Frishauf, Holtz, Goodman & Woodward

[57] ABSTRACT

An apparatus for measuring cardiac output designed to prevent measurement errors by eliminating the need for a manufacture step of examining a temperature sensing element during manufacture of the same and, hence, the need for a probe circuit or the like which is a means for effecting correction according to the characteristics of the temperature sensing element. For measurement of temperatures relating to an organism using a probe having at least two temperature sensing elements, the apparatus includes a reference temperature sensing element; a temperature measurement circuit for obtaining a reference temperature signal from a temperature detected by the reference temperature sensing element; a first temporary storage memory for storing the detected reference temperature; a thermometry temperature sensing element; a second memory for obtaining a thermometry temperature signal with the temperature measurement circuit from a thermometry temperature detected by the thermometry temperature sensing element and for storing the obtained thermometry temperature signal; a correction value calculation circuit for maintaining a correction value obtained on the basis of the reference temperature signal stored in the first memory and the thermometry temperature signal stored in the second memory; and a temperature calculation circuit for calculating a corrected temperature value based on a thermometry temperature signal newly produced during measurement and the maintained correction value.

4 Claims, 3 Drawing Sheets

APPARATUS FOR MEASURING CARDIAC OUTPUT

BACKGROUND OF THE INVENTION

1. Field of the Invention

This invention relates generally to information measuring apparatus and, more particularly, to an an apparatus for measuring cardiac output during and after an operation for a cardiac function test, heart surgery or the like.

2. Description of the Related Art

The applicant of the present invention has disclosed an apparatus for measuring cardiac output in Japanese Patent Laid-Open No. 61-125329. This apparatus has a pair of temperature sensing elements provided in a catheter type sensor probe and operates as described below. The first temperature sensing element is used to detect the temperature of blood to obtain the cardiac output based on a thermodilution method, while the second temperature sensing element is heated up and the temperature thereof is measured to obtain the blood stream velocity. The sectional area of the blood vessel is obtained from the cardiac output based on the thermodilution method and the blood velocity, and the blood velocity is thereafter continuously obtained based on this method with the term of the blood vessel sectional area used as a correction value.

To manufacture temperature sensing elements used in this apparatus, it is necessary to examine the characteristics of thermistors, i.e., the temperature sensing elements. All the temperature sensing elements are therefore placed in a constant temperature bath exposed to an atmosphere of a constant temperature, and the relationship between temperatures and output characteristic values of each temperature sensing element output under this condition is obtained in comparison with a reference thermometer.

On the basis of each of the relationships thereby determined, good articles and inferior articles of the temperature sensing elements are separated from each other, and a probe circuit or the like to be connected to each temperature sensing element is formed to effect compensation for the characteristic values of the temperature, thereby enabling each temperature sensing element to be used for temperature measurement.

Temperature sensing elements for use in measuring apparatus based on the conventional thermodilution method and the conventional thermal type flow measurement method are manufactured in this manner. An additional manufacture step is therefore required along with troublesome management of records of measured characteristic values of respective temperature sensing elements. The problem of reduction in the yield is also encountered.

Moreover, the probe circuit provided as a means for compensating for the characteristic values of the temperature sensing element also entail the problem of variations in its characteristic values and the problem of the characteristic values being changed after it has been connected to the temperature sensing element, resulting in occurrence of measurement errors.

In a case where the temperature is measured by the thermal type flow measurement method apart from the measurement based on the thermodilution method, the characteristics of the temperature sensing element may be influenced by heat during heating of the periphery of the temperature sensing element, resulting in a deterioration in the measurement accuracy.

SUMMARY OF THE INVENTION

The present invention has been achieved in consideration of the above-described problems, and an object of the present invention is to provide an apparatus for measuring cardiac output designed to eliminate the unnecessary step of examining temperature sensing elements used in the apparatus in the process of manufacturing the temperature sensing elements.

Another object of the present invention is to eliminate the need for a probe circuit or the like which is a means for compensating for the characteristic values of a temperature sensing element and to thereby avoid measurement errors.

Still another object of the present invention is to prevent a temperature sensing element from being influenced by heat during heating of the periphery of temperature sensing element based on the thermal type flow measurement method used along with the thermodilution method.

To achieve these objects, according to the present invention, there is provided an apparatus for measuring temperatures relating to an organism by using a probe having at least two temperature sensing elements, the apparatus comprising: a reference temperature sensing element; a temperature measurement circuit means for obtaining a reference temperature signal from a temperature detected by the reference temperature sensing element; a first temporary storage memory means for storing the detected reference temperature; a temperature measurement (thermometry) temperature sensing element; a second memory means for obtaining a temperature measurement temperature signal from the temperature measurement circuit means from a temperature measurement temperature detected by the thermometry temperature sensing element and for storing the obtained thermometry temperature signal; a correction value calculation means for obtaining a correction value based on the reference temperature signal stored in the first memory means and the thermometry temperature signal stored in the second memory means and for maintaining the obtained correction value; and a temperature calculation means for calculating a corrected temperature value based on a thermometry temperature signal newly produced during measurement and the maintained correction value.

DESCRIPTION OF PREFERRED EMBODIMENT

An embodiment of the present invention will be described below with reference to the accompanying drawings.

Figure 1A:
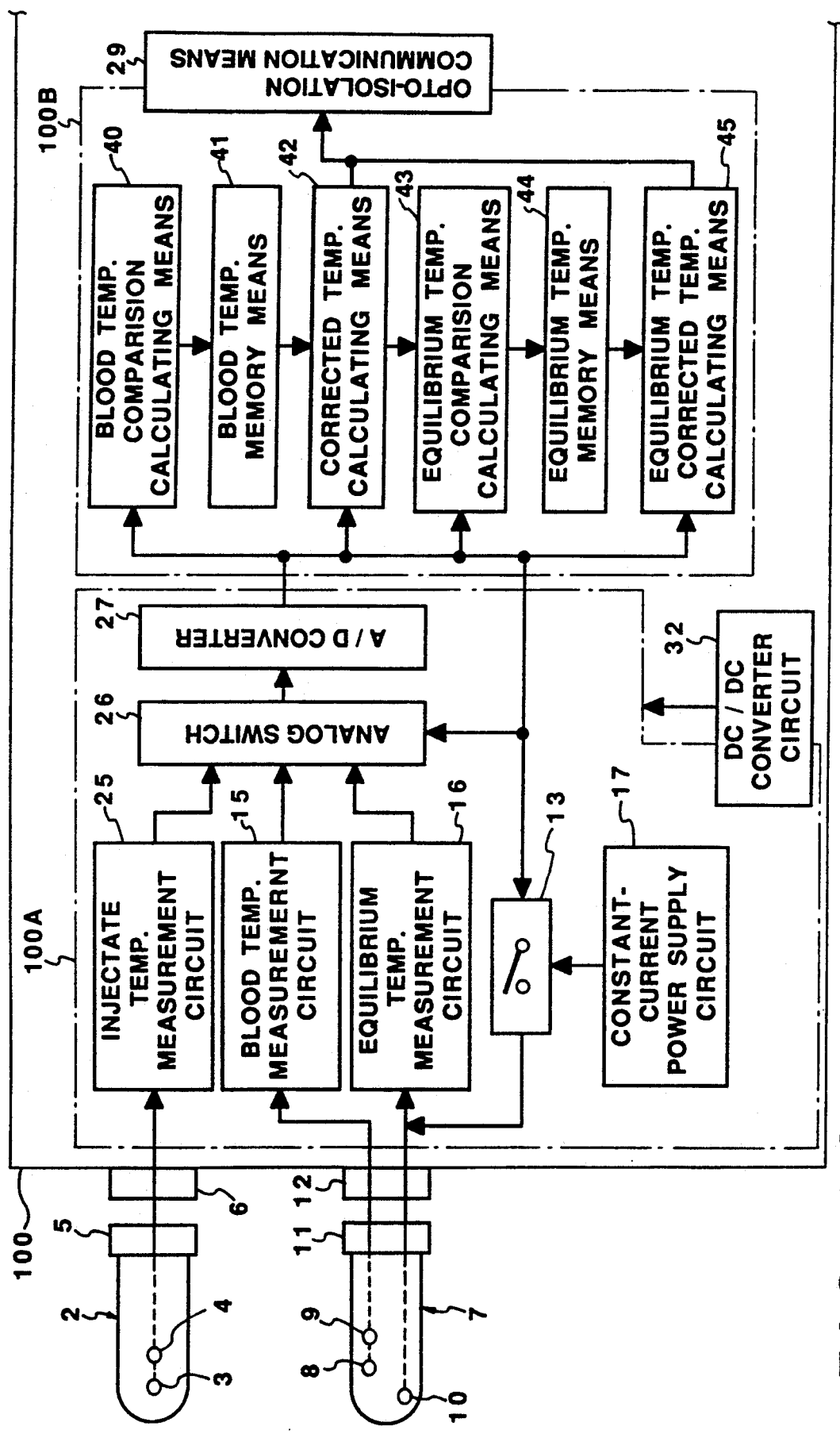
FIG. 1A, 1B are block diagrams of an apparatus for measuring cardiac output which represents an embodiment of the present invention.
Figure 1B:
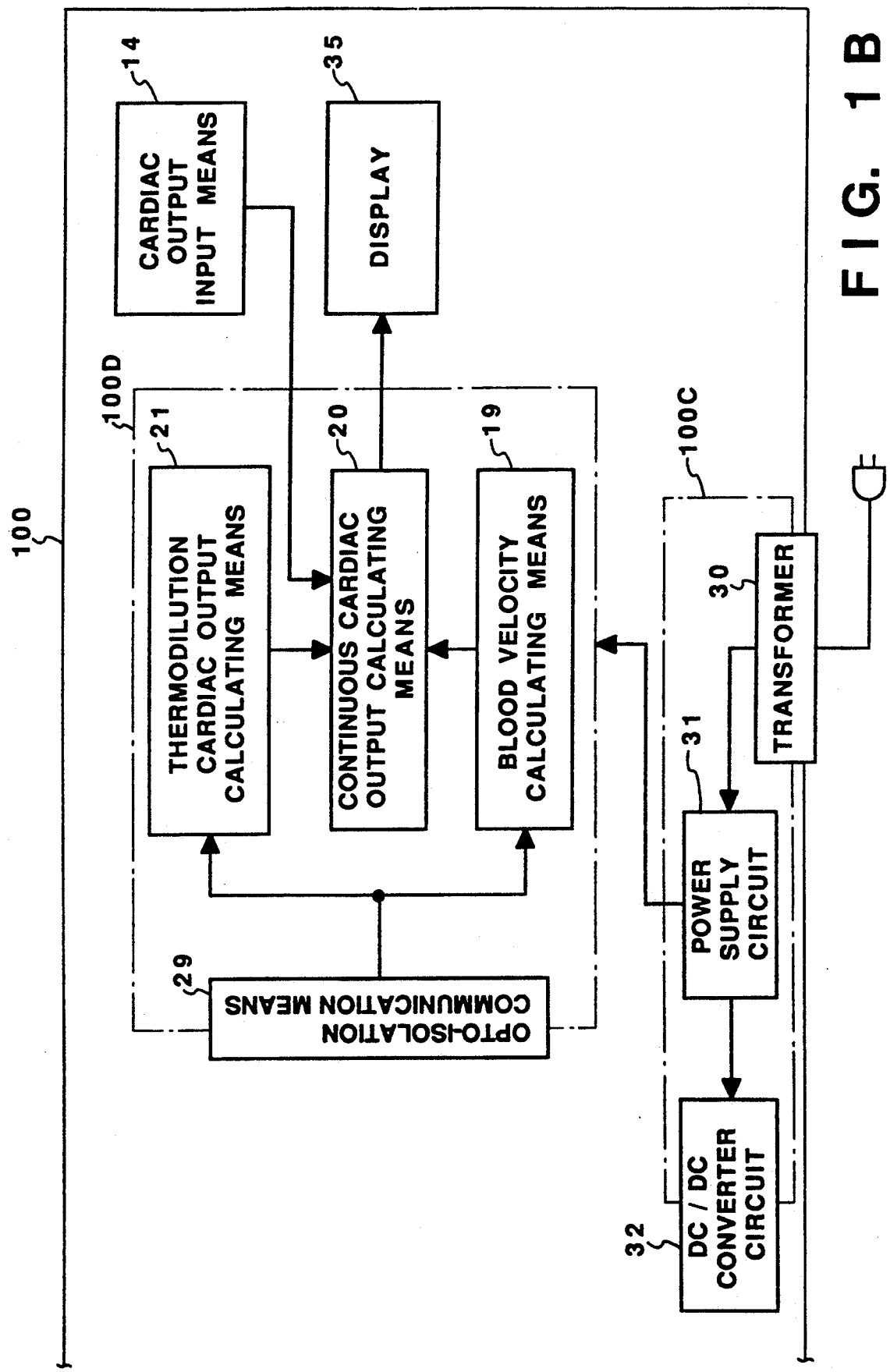

Referring to FIG. 1A and 1B, first and second catheters and 7 for measuring the cardiac output are connected to a main body 100 of the organism information measuring apparatus through connecters described later.

The first catheter 2 is used as a catheter for injecting an injectate based on a thermodilution method and for detecting the temperature of the injectate. The first catheter 2 incorporates an unillustrated injectate temperature measurement probe circuit formed of a temperature sensing element 3 constituted by a thermistor or the like for detecting the temperature of the injectate, and a compensation resistor 4 for compensating for a dispersion in the characteristics of the temperature sensing element 3.

This injectate temperature measurement probe circuit is electrically connected to a measurement section 100A provided in the main body 100 through a connecter 5 of the first catheter 2 and a connecter 6 provided on the main body 100, and is placed in the atrium dextrum of a heart at the time of cardiac output measurement.

The second catheter 7 is used for detecting the temperature of blood and for detecting the blood velocity, and incorporates a blood temperature measurement probe circuit formed of a thermistor 8 for detecting the temperature of thermo-diluted blood in the atrium right and in the ventriculus right and a compensation resistor 9 for compensating for the characteristics of the thermistor 8. The second catheter 7 also incorporates an unillustrated blood velocity temperature measurement probe circuit separately constituted by a thermistor 10 (preferably, a self-heating thermistor) for detecting the blood velocity based on a blood velocity measuring method.

The blood temperature measurement probe circuit and the blood velocity temperature measurement probe circuit are electrically connected to the measurement section 100A provided in the main body 100 through a connecter 11 of the second catheter 7 and a connecter 12 provided on the main body 100, and is placed in the pulmonary artery at the time of cardiac output measurement.

The first and second catheters 2 and 7 may be manufactured so as to be integral with each other in appearance, or the arrangement may be such that only a injectate injector part originally provided in the first catheter 2 is provided integrally with the second catheter 7 while the injectate temperature measurement probe circuit of the first catheter 2 is separately provided and is inserted in an injectate injection tank.

The main body 100 generally consists of the following components: the measurement section 100A connected to the first and second catheters 2 and 7 and serving to effect various temperature measurements; a local CPU section 100B serving to effect correction for the temperature sensing elements; a main CPU section 100D connected to the local CPU section 100B via an opto-isolation communication circuit 29; a cardiac output input means 14; and a display 35.

All the components are electrically separated except for the connection between the measurement section 100A and the local CPU section 100B. Specifically, the main CPU section 100D and the local CPU section 100B are connected through the opto-isolation communication circuit 29, and these sections are supplied with power through a DC/DC converter circuit 32 and are electrically separated from a power supply section 100C, thereby avoiding influence of noise or the like upon various categories of temperature measurement data, as mentioned later.

In the measurement section 100A, an injectate temperature measurement circuit 25 detects the temperature of the injectate injected into the atrium right through an unillustrated injection opening of the first catheter 2, and outputs a corresponding voltage signal.

An equilibrium temperature measurement circuit 16 is connected to a constant-current power supply circuit 17 through a switching device 13, and functions to detect the temperature of equilibrium between the quantity of heat applied by the self-heating thermistor 10 with a constant current and the quantity of heat removed by the effect of the velocity of surrounding blood, and to output a corresponding voltage signal.

A blood temperature measurement circuit 15 is connected to the blood temperature measurement probe circuit, and functions to transmit a reference temperature signal corresponding to the blood temperature to a comparison calculation circuit means provided in the local CPU section 100B. The characteristic values of the thermistor 8, i.e., the temperature sensing element connected to the blood temperature measurement probe circuit are previously examined by employing a reference thermometer and a constant temperature bath. Before the thermistor 10 that is the temperature sensing element of the blood velocity temperature measurement probe circuit is supplied with a current to be heated up, the blood stream velocity temperature measurement probe circuit detects a signal corresponding to the temperature of blood while the switching device 13 is maintained in the off state by an internal command of the local CPU section 100B.

For ordinary measurement, the switching device 13 is turned on by a command from the local CPU section 100B to introduce a current from the constant voltage power supply circuit 17.

When the thermistor 10, i.e., the temperature sensing element of the blood velocity temperature measurement probe circuit is energized for heating, the voltage signal thereby obtained is transmitted as an examined temperature signal to a comparison calculation circuit means 40 provided in the local CPU section 100B.

The reference temperature signal immediately based on the blood temperatures obtained through the blood temperature measurement circuit 15 and the equilibrium temperature measurement circuit 16, an examination signal and the examined temperature signal from the blood velocity temperature measurement probe circuit are transmitted to the blood temperature comparison calculating means 40 via an analog switch 26 and an A/D converter 27.

The blood temperature comparison calculating means 40 calculates differential temperatures based on the comparison between the reference temperature signal and the examined temperature signals, produces signals representing these differential temperatures as a calibration temperature signal for calibration of the blood velocity temperature measurement probe circuit and another calibration temperature signal for calibration of the blood temperature measurement probe circuit, and transmits these signals to a blood temperature memory means 41.

The blood temperature memory means 41 stores a value for calibration of the blood velocity temperature measurement probe circuit and a value for calibration of the blood temperature measurement probe circuit. After a calibration temperature value for the blood temperature measurement probe circuit has been stored by the blood temperature memory means 41, a heating current is made to flow through the temperature sensing element of the blood temperature measurement probe circuit. In this state, the voltage signal output from the blood temperature measurement circuit 15 and the calibration temperature value for the blood temperature measurement probe circuit stored in the blood temperature memory means 41 are transmitted to a correction temperature calculating means 42 as a bias for the same to correct the temperature signal output from the blood temperature measurement circuit 15, thereby ensuring the accuracy of the temperature measurement even when the heating current flows through the temperature sensing element of the blood velocity temperature measurement probe circuit.

The same means as that connected to the blood temperature measurement circuit 15 are provided for the equilibrium temperature measurement circuit 16 to correct the voltage signal output from the equilibrium temperature measurement circuit 16.

The voltage signal output from the equilibrium temperature measurement circuit 16 for the signal representing the temperature detected by the temperature sensing element of the blood velocity temperature measurement probe circuit whose characteristic values are unexamined and the calibration temperature value for the blood velocity probe circuit stored by the blood temperature memory means 41 are transmitted to the correction temperature calculating means 42 as a bias for the same to correct the temperature signal, thereby ensuring the accuracy of the temperature measurement using the temperature sensing element whose characteristic values are unexamined.

The local CPU section 100B supplies the measurement circuits with various control signals transmitted based on instructions of the main CPU section 100D. The local CPU section 100B controls the measurement operations of the injectate temperature measurement circuit 25, the blood temperature measurement circuit 15 and the equilibrium temperature measurement circuit 16 and turns on or off the switching device 13 connected to the constant-current power supply circuit 17. For these operations, the analog switch 26 selects, by selection signals, various signals which are to be supplied to the local CPU 100B.

The local CPU section 100B has a serial communication function (not shown), and receives various command signals transmitted from the main CPU section 100D through this serial communication function. Also, the local CPU section 100B converts digital data received from the measurement circuits into serial transmission data and transmits the converted data to the main CPU section 100D through the opto-isolation communication means 29.

The opto-isolation communication means 29 has a light transmission/reception circuit which is provided on the side of the local CPU section 100B and which consists of a photodiode circuit and a phototransistor circuit (not shown), and another light transmission/reception circuit which is provided on the side of the main CPU section 100D and which also consists of a photodiode circuit and a phototransistor circuit (not shown). These two light transmission/reception circuits being electrically insulated from each other with optical fiber glass or the like interposed therebetween as a signal transmission medium, thereby shutting off electrical noise or the like.

That is, voltage signals of the local CPU section 100B and voltage signals of the main CPU section 100D are prevented from being electrically connected, and there is therefore no possibility of formation of a closed loop between the human body and the main CPU section 100D, thereby make it possible to effect measurement with safety and stability.

In the main CPU section 100D, a thermodilution cardiac output calculating means 21 is supplied with the temperature of thermo-diluted blood, calculates the thermodilution cardiac output, and outputs the result of this calculation to a continuous cardiac output calculating means 20.

If the condition of the patient is so critical that it is not possible to inject the injectate by the thermodilution method, a suitable cardiac output value is input into the continuous cardiac output calculating means 20 through a cardiac output input means 14 as a cardiac output value based on the thermodilution method.

A blood velocity calculating means 19 is continuously supplied with a corrected thermal equilibrium temperature, calculates the blood velocity and outputs the result.

The continuous cardiac output calculating means 20 calculates a blood vessel sectional area parameter of the pulmonary artery based on the blood velocity obtained by the blood velocity calculating means 19 and the thermodilution cardiac output obtained in a thermodilution mode in which the cardiac output is finally output and displayed intermittently by the thermodilution method, and stores the calculated parameter in a register. The continuous cardiac output calculating means 20 then calculates a continuous cardiac output value based on the blood velocity obtained by the blood calculating means 19 and the blood vessel sectional area parameter stored in the register, and outputs the result of this calculation to the display 35 which is connected to the main CPU section 100D and though which the cardiac output is finally output and displayed.

The power supply section 100C for supplying the components with power reduces the voltage of an external AC power supply by means of a transformer 30 connected to the same, and supplies the power supply circuit 31 with power of this reduced voltage. The power supply circuit 31 smooths and stabilizes a predetermined AC output from the transformer 30 to convert the same into a DC voltage and supplies part of the DC power to the DC/DC converter circuit 32. The measurement section 100A and the local CPU section 100B are supplied with DC power from the DC/DC converter circuit 32, and communication of noise between these sections and the main CPU section 100D is therefore shut off.

Figure 2:
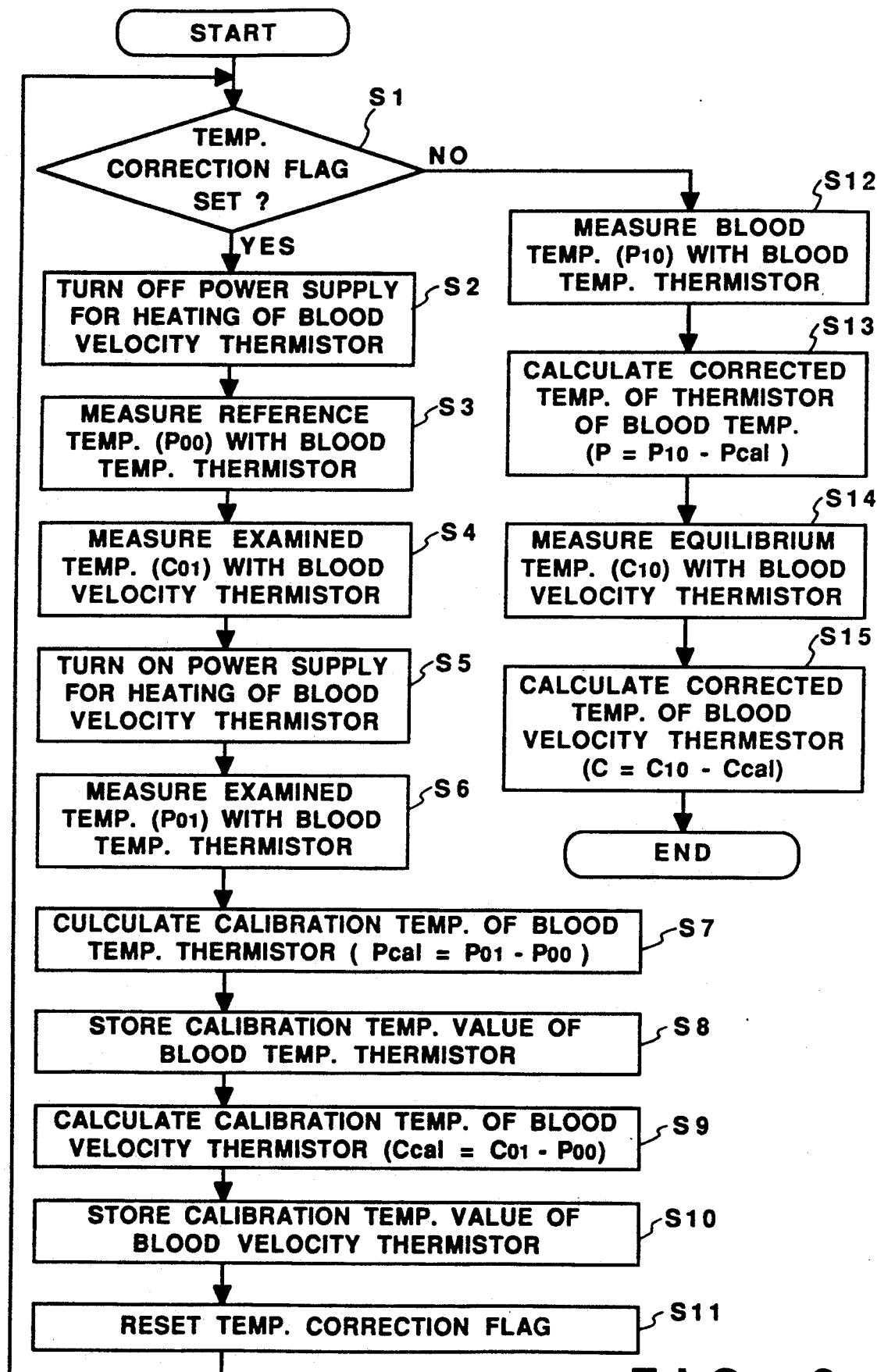
FIG. 2 is a flow chart of a program for temperature correction processing using cardiac output measuring system.

FIG. 2 shows a flow chart of an example of a temperature correction processing program for the cardiac output measuring apparatus. The operation of the apparatus will be described below based on this flow chart. The operation of the temperature correction program is started to confirm whether or not a temperature correction flag is set (step S1), and the switching device 13 is turned off if the flag is set, thereby shutting off the heating current flowing through the thermistor 8 for measuring the blood velocity (step S2).

Then a reference temperature $P_{00}$ is measured by the thermistor 8 and a signal representing this temperature is transmitted as the reference temperature signal to the blood temperature comparison calculation circuit 40 (step S3).

The blood temperature is detected by the thermistor 10 whose characteristic values are unexamined, and the output signal is transmitted as an examined temperature signal $C_{01}$ of the blood velocity temperature measurement probe to the blood temperature comparison calculation circuit 40 (step S4).

Then the switching device 13 is turned on to supply the heating current to the thermistor 10 for measuring the blood velocity (step S5).

Thereafter, a signal $P_{01}$ representing the blood temperature detected by the thermistor 8 is obtained and is transmitted to the blood temperature comparison calculation circuit 40 (step S6).

Next, calculation $P_{cal} = P_{01} - P_{00}$ of the calibration temperature is effected (step S7), and the result of this calculation is stored as the calibration temperature of the blood temperature probe signal in the blood temperature memory means 41 (step S8).

Then calculation $C_{cal} = C_{01} - C_{00}$ of the calibration temperature for the blood velocity thermistor is effected (step S9), and the result of this calculation is stored in the blood temperature memory means 41 (step S10).

After the steps S1 to S10, the temperature correction flag is reset (step S11), and the process returns to step S1.

If it is determined in step S1 that the flag is not set, the process proceeds to step S12, the switching device 13 is turned on, and the blood temperature is measured to obtain a value $P_{10}$.

In step S13, the difference between this value and $P_{cal}$ already obtained is calculated as $P = P_{10} - P_{cal}$. $P$ then becomes the corrected blood temperature.

Thereafter, in step S14, an equilibrium temperature $C_{10}$ is measured and, in step S15, calculation $C = C_{10} - C_{cal}$ is effected by using $C_{cal}$ already obtained. $C$ then becomes the corrected blood velocity temperature. The temperature correction processing program is thus completed.

As described above, it is not necessary to examined and select the temperature sensing element in a strict manner as in the case of the conventional arrangement.

The present invention can be applied to any other type of medical appliance in which temperature sensing elements are used.

As described above in detail, for the organism information measuring apparatus in accordance with the present invention, there is no need for the additional manufacture step of examining the temperature sensing element.

There is no need for a probe circuit or the like which is a means for compensating for the characteristic values of the temperature sensing element, thereby enabling prevention of measurement errors.

Moreover, it is possible to prevent the temperature sensing element from being influenced by heat during heating of the periphery of temperature sensing element based on the thermal type flow measurement method used along with the thermodilution method.

The present invention is not limited to the arrangement of the one embodiment, and various changes and modifications may be made within the spirit and scope of the invention.

What is claimed is:

1. An apparatus for measuring cardiac output relating to an organism, said apparatus comprising:
    probes having at least two temperature sensing elements, said elements including:
    a reference temperature sensing element whose temperature characteristics are known; and
    a thermometry temperature sensing element whose temperature characteristics are unknown;
    temperature measurement circuit means for measuring a reference temperature signal from a temperature detected by said reference temperature sensing element, and for producing a measured reference temperature signal;
    first temporary storage memory means for storing the measured reference temperature signal;
    said temperature measurement circuit means including means for producing a thermometry temperature signal from a thermometry temperature detected by said thermometry temperature sensing element;
    second memory means for storing said thermometry temperature signal;
    correction value calculation means for calculating a correction value responsive to the reference temperature signal stored in said first temporary storage memory means and the thermometry temperature signal stored in said second memory means, and for maintaining the calculated correction value;
    temperature calculation means for calculating a corrected temperature value as a function of a thermometry temperature signal newly produced during measurement and the maintained calculated correction value;
    switching means for selectively connecting said reference temperature sensing element and said thermometry temperature sensing element to said temperature measurement circuit means; and
    cardiac output measuring means for measuring cardiac output responsive to the calculated corrected temperature value from said temperature calculation means.

2. An apparatus for measuring cardiac output according to claim 1, wherein said cardiac output measurement means includes means for measuring said cardiac output based on a thermodilution method and a thermal type flow measurement method.

3. An apparatus for measuring cardiac output according to claim 1, further comprising:
    heating means for heating up the periphery of said thermometry temperature sensing element to obtain a heated temperature signal through said temperature measurement circuit means;
    memory means for storing the obtained heated temperature signal;
    said correction value calculation means including means for calculating a correction value from the reference temperature signal and the heated temperature signal;
    said temperature calculation means calculates a corrected temperature value based on a newly produced heated temperature signal, different from said first-mentioned heated temperature signal, and the calculated correction value, said newly produced heated temperature signal being produced during subsequent measurement; and
    comparison calculation means for calculating a temperature based on the calculated correction value.

4. An apparatus for measuring cardiac output according to claim 3, wherein said heating means for heating up said thermometry temperature sensing element includes power supply means for supplying power to said thermometry temperature sensing element.

* * * * *

UNITED STATES PATENT AND TRADEMARK OFFICE
CERTIFICATE OF CORRECTION

PATENT NO. : 5,080,106
DATED : January 14, 1992
INVENTOR(S) : SEKII et al

It is certified that error appears in the above-identified patent and that said Letters Patent is hereby corrected as shown below:

Column 1, line 7, following "generally to", insert -- an --.

Column 2, lines 62-63, following "catheters", insert -- 2 --.

Column 7, line 34, change "examined" to -- examine --.

Signed and Sealed this

Fifteenth Day of February, 1994

Attest:

BRUCE LEHMAN

Attesting Officer   Commissioner of Patents and Trademarks